(12) United States Patent
Skujins et al.

(10) Patent No.: US 6,918,882 B2
(45) Date of Patent: Jul. 19, 2005

(54) GUIDEWIRE WITH STIFFNESS BLENDING CONNECTION

(75) Inventors: Peter Skujins, Minneapolis, MN (US); Brian Reynolds, Ramsey, MN (US); Greg Schultz, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 95 days.

(21) Appl. No.: 09/972,276

(22) Filed: Oct. 5, 2001

(65) Prior Publication Data

US 2003/0069520 A1 Apr. 10, 2003

(51) Int. Cl.$^7$ .......................... A61B 5/00; A61M 25/00
(52) U.S. Cl. ...................................... 600/585; 604/533
(58) Field of Search ................................ 600/433–435, 600/585; 604/523–535

(56) References Cited

U.S. PATENT DOCUMENTS

| | | | |
|---|---|---|---|
| 4,080,706 A | 3/1978 | Heilman et al. | |
| 4,456,017 A | 6/1984 | Miles | |
| 4,538,622 A | 9/1985 | Samson et al. | |
| 4,556,240 A | * 12/1985 | Yoshida ........................ | 285/55 |
| 4,763,647 A | 8/1988 | Gambale | |
| 4,813,434 A | 3/1989 | Buchbinder et al. | |
| 4,846,186 A | 7/1989 | Box et al. | |
| 4,884,579 A | 12/1989 | Engelson | |
| 4,925,445 A | 5/1990 | Sakamoto et al. | |
| 4,984,581 A | 1/1991 | Stice | |
| 5,069,226 A | 12/1991 | Yamauchi et al. | |
| 5,109,867 A | * 5/1992 | Twyford, Jr. ................ | 600/585 |
| 5,111,829 A | 5/1992 | Alvarez de Toledo | |
| 5,213,111 A | 5/1993 | Cook et al. | |
| 5,238,004 A | 8/1993 | Sahatjian et al. | |
| 5,273,052 A | 12/1993 | Kraus et al. | |
| 5,275,173 A | 1/1994 | Samson et al. | |
| 5,312,356 A | 5/1994 | Engelson et al. | |
| 5,333,620 A | 8/1994 | Moutafis et al. | |
| 5,341,818 A | 8/1994 | Abrams et al. | |
| 5,365,943 A | 11/1994 | Jansen | |
| 5,402,829 A | * 4/1995 | Takikawa et al. ........... | 138/109 |
| 5,411,476 A | 5/1995 | Abrams et al. | |
| 5,433,200 A | 7/1995 | Fleischhacker, Jr. | |
| 5,452,726 A | 9/1995 | Burmeister et al. | |
| 5,637,089 A | 6/1997 | Abrams et al. | |
| 5,651,373 A | 7/1997 | Mah | |
| 5,695,111 A | 12/1997 | Nanis et al. | |
| 5,772,641 A | 6/1998 | Wilson | |
| 5,782,776 A | 7/1998 | Hani | |
| 5,797,857 A | 8/1998 | Obitsu | |
| 5,820,571 A | 10/1998 | Erades et al. | |
| 5,833,631 A | 11/1998 | Nguyen | |
| 5,836,893 A | 11/1998 | Urick | |
| 5,980,471 A | 11/1999 | Jafari | |
| 6,001,068 A | 12/1999 | Uchino et al. | |
| 6,042,553 A | 3/2000 | Solar et al. | |
| 6,106,488 A | 8/2000 | Fleming et al. | |
| 6,165,292 A | 12/2000 | Abrams et al. | |
| 6,168,571 B1 | 1/2001 | Solar et al. | |

(Continued)

FOREIGN PATENT DOCUMENTS

| | | |
|---|---|---|
| EP | 0 274 412 | 7/1988 |
| EP | 0 491 349 | 6/1992 |
| EP | 0 806 220 | 11/1997 |
| EP | 0 838 230 | 4/1998 |
| WO | WO 00/402860 | 7/2000 |

*Primary Examiner*—Charles Marmor
(74) *Attorney, Agent, or Firm*—Crompton, Seager & Tufte

(57) ABSTRACT

Alternative designs and materials suitable for connecting different guidewire sections together. More particularly, connecting two portions of a guidewire having different material compositions with a connector having a third composition which is readily weldable to each of the dissimilar portions of the guidewire. A transition area may be designed to provide a region of desired flexibility characteristics.

15 Claims, 3 Drawing Sheets

U.S. PATENT DOCUMENTS

| | | |
|---|---|---|
| 6,183,420 B1 | 2/2001 | Douk et al. |
| 6,234,981 B1 | 5/2001 | Howland |
| 6,248,082 B1 | 6/2001 | Jafari |
| 6,306,105 B1 | 10/2001 | Rooney et al. |
| 6,352,515 B1 | 3/2002 | Anderson et al. |
| 6,464,651 B1 * | 10/2002 | Hiejima et al. ............. 600/585 |
| 6,497,709 B1 | 12/2002 | Health |
| 6,554,942 B2 | 4/2003 | Solar et al. |
| 6,561,218 B2 * | 5/2003 | Mudd ....................... 137/487.5 |
| 6,610,046 B1 | 8/2003 | Usami et al. |
| 6,682,493 B2 | 1/2004 | Mirigian |

* cited by examiner

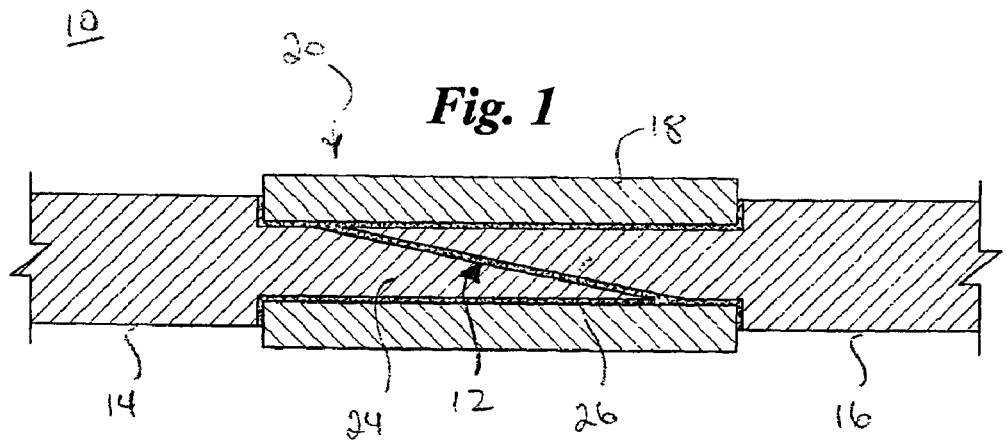
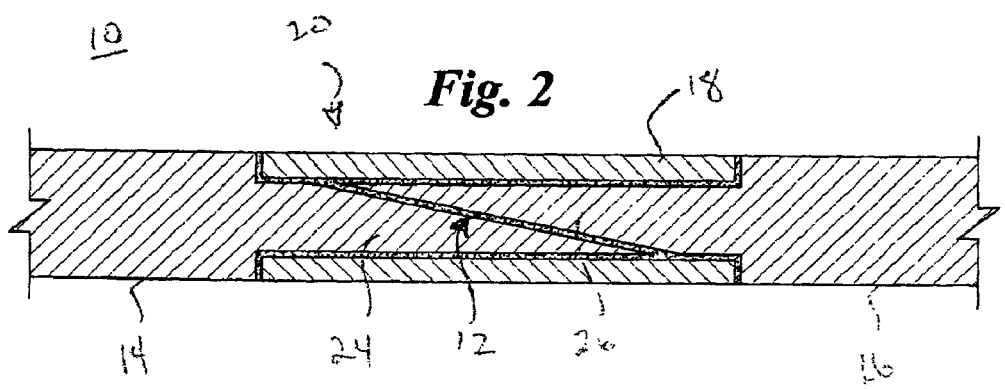
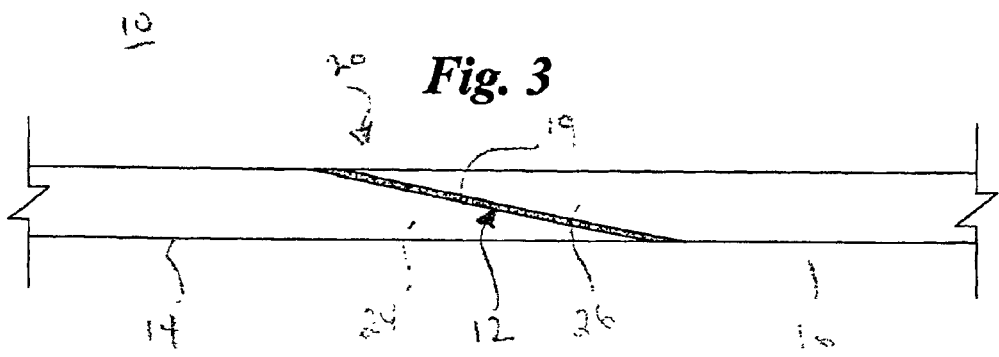

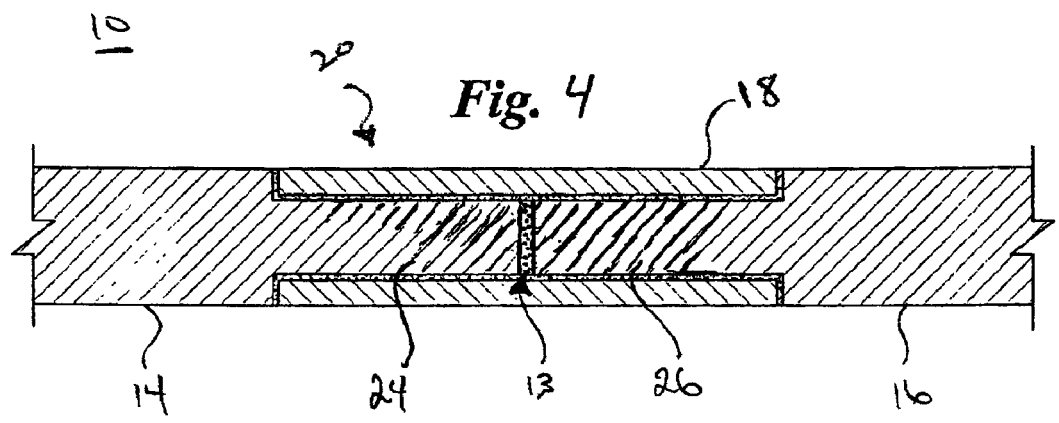

GUIDEWIRE WITH STIFFNESS BLENDING CONNECTION

FIELD OF THE INVENTION

The present invention generally pertains to intravascular guidewires.

BACKGROUND OF THE INVENTION

Intravascular guidewires are commonly used in conjunction with intravascular devices such as balloon catheters to facilitate navigation through the vasculature of a patient. Because the vasculature of a human being may be very tortuous, guidewires often have a stiff proximal portion for pushability and torqueability, and a flexible distal portion for trackability.

SUMMARY OF THE INVENTION

To provide for a relatively stiff proximal portion and a relatively flexible distal portion, the proximal and distal portions of the guidewire may be formed of different materials. The present invention provides several alternative designs, materials and manufacturing methods for connecting different guidewire sections together.

BRIEF DESCRIPTION OF THE DRAWINGS

FIG. 1 is cross sectional fragmentary view of a guidewire (pre-grinding), including a connection utilizing an overlapping tapered joint and a tubular connector for joining a proximal section and a distal section of the guidewire;

FIG. 2 is a cross sectional fragmentary view of the guidewire (post grinding) of FIG. 1;

FIG. 3 is a cross sectional fragmentary view of an alternative guidewire (post grinding), including a connection utilizing an overlapping joint (without a tubular connector) for joining a proximal section and a distal section of the guidewire;

FIG. 4 is a cross sectional fragmentary view of an alternative guidewire (post grinding), including a connection utilizing a butt joint and a tubular connector for joining a proximal section and a distal section of the guide wire;

DETAILED DESCRIPTION OF THE INVENTION

Figure 5:
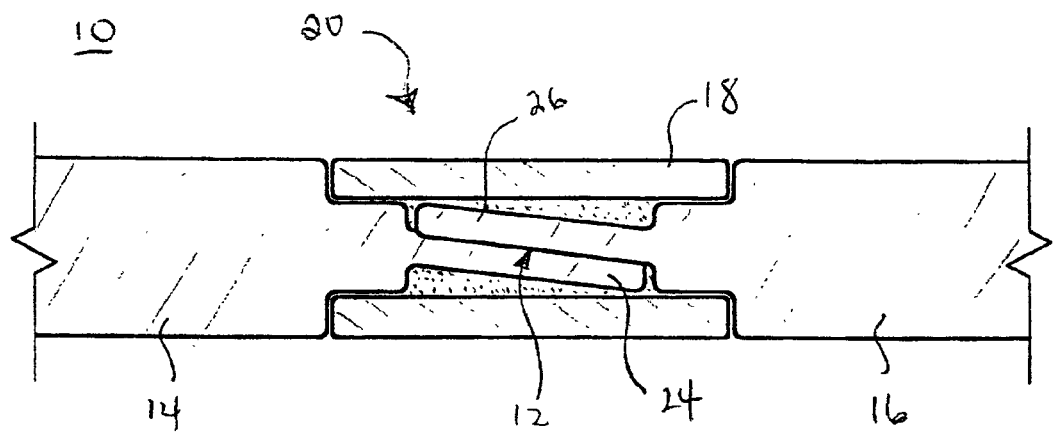
FIG. 5 is a cross sectional fragmentary view of an alternative guidewire (post grinding), including a connection utilizing an overlapping joint and a tubular connector for joining a proximal section and a distal section of the guide wire.

The following description should be read with reference to the drawings wherein like reference numerals indicate like elements throughout the several views. The detailed description and drawings illustrate examples of various embodiments of the claimed invention, and are not intended to be limiting.

Refer now to FIGS. 1–5 which illustrate cross sectional views of a portion of a guidewire 10 including a connection 20 joining a proximal guidewire section 14 and a distal guidewire section 16. FIG. 1 illustrates the guidewire 10 and the connection 20 before a final grinding step, and FIG. 2 illustrates the guidewire 10 and the connection 20 after the final grinding step, which provides a smooth outer profile. The embodiment of FIGS. 1 and 2 utilizes an overlapping tapered joint 12 and a tubular connector 18.

The embodiment of FIG. 3 is similar to the embodiment of FIGS. 1 and 2, except that the connection 20 between the proximal guidewire section 14 and the distal guidewire section 16 does not utilize a connector tube 18, but rather utilizes a connector material 19. The embodiment of FIG. 4 is similar to the embodiment of FIGS. 1 and 2, except that the connection 20 between the proximal guidewire section 14 and the distal guidewire section 16 does not utilize an overlapping joint 12, but rather uses a butt joint 13. The embodiment of FIG. 5 is also similar to the embodiment of FIGS. 1 and 2, except that the connection 20 between the proximal guidewire section 14 and the distal guidewire section 16 utilizes an overlapping joint 12 that is not tapered.

The proximal and distal guidewire sections 14/16 may have a solid cross-section as shown, or a hollow cross-section, and may be formed of metals or metal alloys suitable for metal joining techniques such as welding, soldering, brazing, crimping, friction fitting, adhesive bonding, etc. As used herein, the proximal section 14 and the distal section 16 may generically refer to any two adjacent guidewire sections along any portion of the guidewire. Furthermore, although discussed with specific reference to guidewires, the present invention may be applicable to almost any intravascular device having two adjacent metallic shaft sections. For example, the present invention may be applicable to metallic hypotube shafts for intravascular catheters (e.g., rapid exchange balloon catheters, stent delivery catheters, etc.) or metallic drive shafts for intravascular rotational devices (atherectomy catheters, IVUS catheters, etc.).

The proximal guidewire section 14 may be formed of relatively stiff material such as straightened 304v stainless steel wire. Alternatively, proximal portion 14 may be comprised of a metal or metal alloy such as a nickel-titanium alloy, nickel-chromium alloy, nickel-chromium-iron alloy, cobalt alloy, or other suitable material. In general, the material used to construct proximal portion 14 may be selected to be relatively stiff for pushability and torqueability.

The distal guidewire section 16 may be formed of a relatively flexible material such as a straightened super elastic or linear elastic alloy (e.g., nickel-titanium) wire. Alternatively, distal portion 16 may be comprised of a metal or metal alloy such as stainless steel, nickel-chromium alloy, nickel-chromium-iron alloy, cobalt alloy, or other suitable material. In general, the material used to construct distal portion 16 may be selected to be relatively flexible for trackability.

Figure 6A:
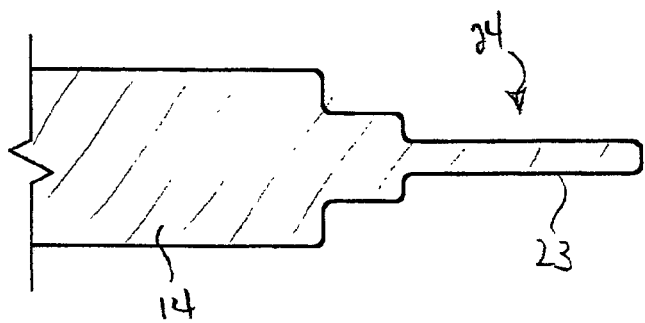
FIGS. 6A–6C are cross sectional fragmentary views of various end portions for use with the guidewire embodiment of FIG. 5.
Figure 6B:
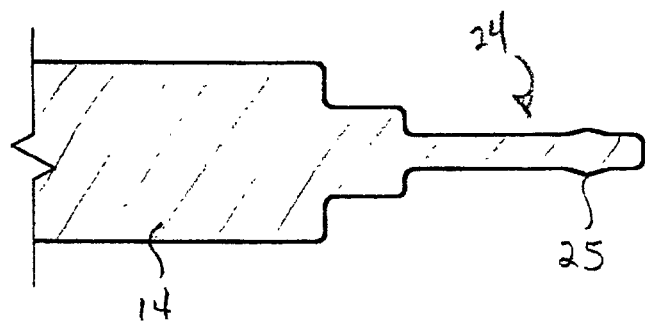
Figure 6C:
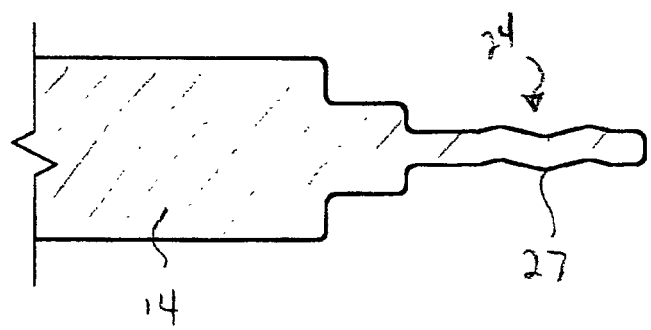

The distal end 24 of the proximal portion 14 and the proximal end 26 of distal portion 16 (i.e., the joined ends) may form an overlapping tapered joint 12 as shown in FIGS. 1–3. Alternatively, the joined ends 24/26 may form a butt joint 13 as shown in FIG. 4. As a further alternative, the joined ends 24/26 may form an overlapping joint 12 that is not tapered as shown in FIG. 5. The non-tapered end portions 24/26 may have a uniform profile (diameter) 23 as shown in FIG. 6A, a bulbous portion 25 for purposes of mechanical interlocking as shown in FIG. 6B, or a helical form 27 for purposes of mechanical interlocking as shown in FIG. 6C. In each of the embodiments illustrated in FIGS. 1–3 and 5, the end portions 24/26 overlap to form an overlapping joint 12. The overlapping joint 12 blends the stiffness of proximal portion 14 and distal portion 16 by combining the properties of each end section 24/26 making up the cross section of the overlapping joint 12. Thus, the joint 12 forms a flexibility transition region that has a relative flexibility that is between the flexibility of the proximal portion 14 and the flexibility of the distal portion 16.

In the tapered embodiments illustrated in FIGS. 1–3, the ends 24/26 may be tapered or otherwise formed to have a mating geometry, wherein the cross-sectional area of each end section 24/26 gradually decreases toward the middle of the connection 20. The tapered overlapping portion 12 may define a uniform or a non-uniform transition of the sections 24/26, depending on the transition characteristics desired. For example, the end sections 24/26 may be linearly tapered as shown, tapered in a curvilinear fashion, or tapered in a step-wise fashion. If tapered linearly as shown, the angle of the taper may vary. Using the longitudinal center axis of the guidewire 10 as a reference, as measured from the extreme ends of the end sections 24/26, the angle of the taper is acute (i.e., less than 90 degrees), and may be in the range of 5 degrees to 45 degrees, for example. Varying the angle of the tapered ends 24/26 also varies the length of the overlapping joint 12 in accordance with geometric principles. The length of the overlapping joint 12 may be selected to obtain a more (longer length) or less (shorter length) gradual transition in stiffness.

As mentioned previously, the proximal guidewire section 14 and the distal guidewire section 16 may be formed of different materials (i.e., materials having different moduli of elasticity) resulting in a difference in flexibility. For example, the proximal guidewire section 14 may be formed of stainless steel wire and the distal guidewire section 16 may be formed of nickel-titanium alloy wire, both having the same dimensions, resulting in a 3:1 difference in elastic modulus. Such a difference in elastic modulus (i.e., flexibility) may result in a stress concentration point during flexure and/or torsion that may have a tendency to kink. By virtue of the gradual transition in stiffness provided by the overlapping portion 12, stress is distributed along the entire length of the connection 20 thereby decreasing the probability that guidewire 10 may kink at the junction.

A gradual transition in stiffness may also allow the connection 20 to be located further distally. According to this embodiment, the distal portion 16 may be manufactured to be shorter than proximal portion 14. Including a relatively long proximal section 14 may advantageously increase the torquability and pushability of the guidewire 10. Although only one connection 20 is shown, additional connections 20 may be used to connect other guidewire sections of varying stiffness.

The connector 18 may comprise a tubular structure such as a hypotube as shown or a coiled wire. The connector 18 may have an inside diameter sized appropriately to receive the ends 24/26 of the proximal portion 14 and the distal portion 16, and an outside diameter sufficient to accommodate a final grinding procedure. The final diameter of the guidewire 10 and the connector 18 may be in the range of 0.010 to 0.018 inches, for example. By way of example, not limitation, the connector 18 may have a length of about 1.0 to 3.0 inches for an overlapping portion 12 of about 0.75 to 2.5 inches.

The connector 18 may be comprised of a metal or metal alloy, and may include radiopaque materials. Suitable metals and metal alloys include stainless steels, nickel-titanium alloys (e.g., nitinol), nickel-chromium alloys, nickel-chromium-iron alloys, cobalt alloys, nickel, or other suitable materials. Alternatively, connector 18 may be comprised of a polymer or a metal-polymer composite, including a radiopaque filler.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Some types of alloys are particularly suitable for connector 18 for purposes of connecting a stainless steel proximal section 14 and a nickel titanium alloy distal section 16, or visa-versa. An example is a nickel-chromium-iron alloy available under the trade name INCONEL 625, which advantageously welds to both stainless steels and nickel-titanium alloys. INCONEL 625 may be obtained from California Fine Wire Company of Grover Beach, Calif., and has the following composition:

| Material | Symbol | % by wat |
| --- | --- | --- |
| Aluminum | Al | 0.140 |
| Carbon | C | 0.070 |
| Chromium | Cr | 21.900 |
| Cobalt | Co | 0.010 |
| Copper | Cu | 0.030 |
| Iron | Fe | 2.790 |
| Manganese | Mn | 0.030 |
| Molybdenum | Mo | 9.150 |
| Nickel | Ni | 62.000 |
| Niobium | Nb | 3.540 |
| Phosphorus | P | 0.005 |
| Silicon | Si | 0.230 |
| Sulfur | S | 0.009 |
| Titanium | Ti | 0.250 |
| Tantalum | Ta | 0.010 |

Another example of a suitable alloy which welds to both stainless steels and nickel-titanium alloys is available under the trade name ALLOY C276 from Fort Wayne Metals Research Products Corporation of Fort Wayne, Ind., which has the following composition:

| Material | Symbol | % by wat |
| --- | --- | --- |
| Carbon | C | 0.003 |
| Chromium | Cr | 15.810 |
| Cobalt | Co | 1.310 |
| Copper | Cu | 0.100 |
| Iron | Fe | 5.730 |
| Manganese | Mn | 0.520 |
| Molybdenum | Mo | 16.010 |
| Nickel | Ni | 57.000 |
| Phosphorus | P | 0.008 |
| Silicon | Si | 0.020 |
| Sulfur | S | 0.005 |
| Tungsten | W | 3.570 |
| Vanadium | V | 0.160 |

Another example of a suitable alloy which welds to both stainless steels and nickel-titanium alloys is available under the trade name ALLOY B2 from Fort Wayne Metals Research Products Corporation of Fort Wayne, Ind., which has the following composition:

| Material   | Symbol | % by wat |
|------------|--------|----------|
| Carbon     | C      | 0.005    |
| Chromium   | Cr     | 0.450    |
| Cobalt     | Co     | 0.110    |
| Copper     | Cu     | 0.030    |
| Iron       | Fe     | 1.410    |
| Manganese  | Mn     | 0.150    |
| Molybdenum | Mo     | 27.720   |
| Nickel     | Ni     | 70.000   |
| Phosphorus | P      | 0.004    |
| Silicon    | Si     | 0.020    |
| Sulfur     | S      | 0.002    |
| Tungsten   | W      | 0.140    |

To manufacture the connection 20 of the guidewire 10, the ends 24/26 of the proximal and distal guidewire sections 14/16 may be ground to form the desired shape (e.g., uniform diameter 23, bulbous portion 25, helix 27, or taper) to accommodate the overlapping joint 12. If a butt joint 13 is to be used, such a shape need not be ground. A recess step may be ground into the proximal and distal guidewire sections 14/16 to accommodate the connector tube 18. If a connector tube 18 is not to be used, such a recess step need not be ground.

For the embodiments utilizing a connector tube 18, the connector tube 18 is positioned over one of the ends 24/26 of the proximal and distal guidewire sections 14/16. The distal end 24 of the proximal portion 14 and proximal end 26 of the distal portion 16 are then positioned adjacent one another in an overlapping 12 or an end-to-end 13 arrangement. The proximal and distal guidewire sections 14/16 and the connector tube 18 may be bonded, welded (e.g., resistance or laser welded), soldered, brazed, or otherwise connected by a suitable technique depending on the material selected for each component. Alternatively, the ends 24/26 and the connector tube 18 may be crimped together or may be sized to establish a friction fit therebetween. If a connector tube 18 is not used, the ends 24/26 may be bonded, welded (e.g., resistance or laser welded), soldered, brazed, or otherwise connected, using a connector material 19. Connector material 19 may be the same as or similar to the material of the connector 18. In all cases, because the connection 20 may reside within a catheter lumen during use, it is preferred that a permanent connection (as opposed to a releasable connection) be used.

It is to be appreciated that various welding processes may be utilized without deviating from the spirit and scope of the present invention. Examples of welding processes which may be suitable in some applications include LASER welding, resistance welding, TIG welding, microplasma welding, electron beam, and friction or inertia welding. LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

Once connected, the connector tube 18 and the proximal and distal guidewire sections 14/16 are centerless ground to provide a smooth and uniform profile across the connection 20, and to straighten out small misalignments between the proximal and distal guidewire sections 14/16. Other portions of the guidewire 10 may be ground as well to provide the desired tapers and changes in diameter. Once finally ground, a flexible coil tip and/or a polymer jacket (optionally covering connection 20) may be placed on the guidewire 10, and a lubricious coating (e.g., hydrophylic) may be applied.

The centerless grinding technique may utilize an indexing system employing sensors (e.g., optical/reflective, magnetic) to avoid excessive grinding of the connection 20. In addition, the centerless grinding technique may utilize a CBN or diamond abrasive grinding wheel that is well shaped and dressed to avoid grabbing the connector 20 during the grinding process.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A guidewire, comprising:
    a proximal section having a distal portion, the proximal section comprising a first material, wherein the first material comprises stainless steel;
    a distal section having a proximal portion, the distal section comprising a second material, wherein the second material comprises a nickel-titanium alloy; and
    a connector disposed adjacent and welded to the distal portion of the proximal section and the proximal portion of the distal section, the connector comprising a third material different from the first material and the second material, the third material comprising nickel-chromium-molybdenum alloy, C276, or B2 alloy that is compatible for welding to both stainless steel and nickel-titanium alloy.

2. A guidewire as in claim 1, wherein the proximal section has a first flexibility and the distal section has a second flexibility, and wherein the distal portion of the proximal section and the proximal portion of the distal section overlap to define a region that blends the first flexibility with the second flexibility.

3. A guidewire as in claim 1, wherein the distal portion of the proximal section has a reduced size portion and the proximal portion of the distal section has a reduced size portion.

4. A guidewire as in claim 3, wherein the reduced size portions have a taper.

5. A guidewire as in claim 3, wherein the reduced size portions have an interlocking shape.

6. A guidewire as in claim 3, wherein at least a portion of the connector is disposed between the reduced size distal portion of the proximal section and the reduced sized proximal portion of the distal section.

7. A guidewire as in claim 1, wherein the third material comprises a nickel-chromium-iron alloy.

8. A guidewire as in claim 1, wherein the connector comprises a tubular member disposed about the distal portion of the proximal section and the proximal portion of the distal section.

9. A guidewire as in claim 8, wherein the tubular connector has an outside diameter that is the same as an outside diameter of the proximal section.

10. A guidewire as in claim 9, wherein the tubular connector has an outside diameter that is the same as an outside diameter of the distal section.

11. A guidewire, comprising:
- a proximal section having a distal portion, the proximal section comprising stainless steel;
- a distal section having a proximal portion, the distal section comprising a nickel-titanium alloy; and
- a connector disposed adjacent and welded to the distal portion of the proximal section and the proximal portion of the distal section, the connector comprising a nickel-chromium-molybdenum alloy.

12. A guidewire as in claim 11, wherein the proximal section has a first flexibility transition region having a first flexibility and the distal section has a second flexibility transition region having a second flexibility, and wherein flexibility transition regions overlap to define a region that blends the first flexibility with the second flexibility.

13. A guidewire as in claim 12, wherein at least a portion of the connector is disposed between the flexibility transition regions.

14. A guidewire as in claim 11, wherein the connector comprises a nickel-chromium-molybdenum-iron alloy tube.

15. A guidewire, comprising:
- a proximal section comprising stainless steel;
- a distal section comprising nickel-titanium alloy; and
- a connector comprising a nickel-chromium-molybdenum alloy which is welded to and connects the proximal and distal sections.

* * * * *